Feb. 18, 1969 J. A. LONG Plant Pat. 2,864

ST. AUGUSTINEGRASS

Filed May 15, 1967

INVENTOR
John A. Long
by Strauch, Nolan, Neale, Nies & Kurz
ATTORNEYS

United States Patent Office

Plant Pat. 2,864

Patented Feb. 18, 1969

2,864

ST. AUGUSTINE GRASS

John A. Long, Marysville, Ohio, assignor to The O. M. Scott & Sons Company, Marysville, Ohio, a corporation of Ohio

Filed May 15, 1967, Ser. No. 638,673
U.S. Cl. Plt.—88 1 Claim
Int. Cl. A01h *5/12*

ABSTRACT OF THE DISCLOSURE

A variety of perennial St. Augustine grass having outstanding resistance to chinch bugs, pleasing, moderate yellow green color and a stocky leaf blade. The variety is highly competitive with weeds, easily propagated, resistant to nematodes, vigorous, rugged, tolerant to commercial pesticides, and has a high rate of horizontal growth.

*Summary of the variety*

This invention relates to a new and distinct variety of perennial St. Augustine grass plant, originally selected from a series of hybrids cultivated under greenhouse conditions and resulting from cross pollination of a purple stigma male parent (progeny selection made from Variegatum) and a white stigma female parent (progeny selection from Texas common). The original plant material was vegetatively propagated by stolons and installed in field plots for evaluation. This St. Augustine grass plant was labeled Ea 6416.

Ea 6416 St. Augstine grass has several distinctive characteristics not evident in other St. Augstine grasses. The most desirable of these is its vigor. Others are a, pleasing, moderate olive green color similar to that of Bitter Blue St. Augustine grass, high resistance to chinch bugs, good competitiveness with weeds in turfs in which it is planted, ease of propagation, stocky leaf blades, short ground hugging plants, resistance to nematodes, high degree of tolerance to commercial pesticides and energetic horizontal growth, which makes the fast establishment of a new turf possible.

The aforementioned desirable and unique qualities make Ea 6416 St. Augustine grass an outstanding turfgrass. Because of its vigor of growth and competitiveness, it makes a dense, rugged turf with good traffic wearing qualities. Furthermore, its high density provides a desirable cushionlike resilience.

Because of its, pleasing color, Ea 6416 provides an aesthetic turf. Additionally, its stout leaf texture imparts a desirable luxuriant quality and appearance to the turf.

The outstanding resistance of Ea 6416 St. Augustine grass to damage from chinch bugs and sting nematodes contributes materially to its excellent performance. This characteristic is of importance to vigor of the plant throughout the season. The inherent resistance to damage from these pests also extends the season of grass enjoyment and lessens the maintenance procedures and costs of providing peticides for protection from these pests.

It is my primary object to provide a St. Augustine grass plant having the desirable characteristics mentioned above and described in detail below. Other objects will become apparent to those skilled in the relevant arts from the appended claim and from the following description in conjunction with the accompanying illustrations of Ea 6416 St. Augustine grass.

*Brief description of the illustrations*

*Detailed description of the variety*

Figure 1:
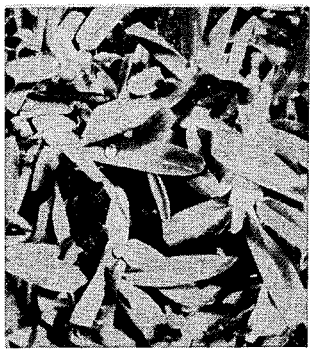
FIGURE 1 is a picture of Ea 6416 St. Augustine turf showing generally the characteristics of this new variety.
Figure 2:
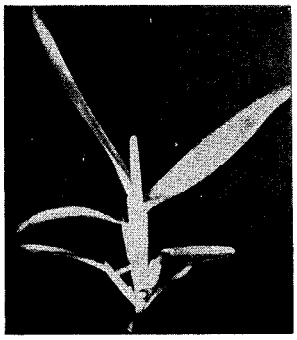
FIGURE 2 shows the leaves and stem of an Ea 6416 St. Augustine grass plant.
Figure 3:
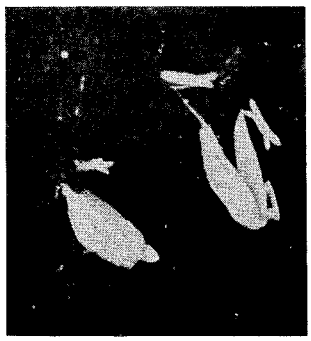
FIGURE 3 shows the stigma color and spikelet characteristics of Ea 6416 St. Augstine grass.

Ea 6416 St. Augustine grass (*Stenotaphrum secundatum*) is distinguished from Floratine and Bitter Blue St. Augustine grasses by its chromosome number in that Ea 6416 St. Augustine has a chromosome number of 18 and Floratine and Bitter Blue St. Augustine grasses each have chromosome numbers of 27. Ea 6416 St. Augustine grass is characterized by a purple stigma as contrasted to the widely grown Texas common St. Augustine grass which has white stigmas. The chromosome numbers and stigma colors of Ea 6416 and other St. Augustine grasses are compared in Table 1.

TABLE 1.—CHROMOSOME NUMBERS AND STIGMA COLORS OF Ea 6416 ST. AUGUSTINE GRASS AND OTHER ST. AUGUSTINE GRASSES

| Selection/variety | Chromosome No. (unreduced) [1] | Stigma color |
|---|---|---|
| Ea 6416 | 18 | Purple. |
| PI 243552 [2] | 18 | Do. |
| Texas common | 18 | White |
| Floratine | 27 | Purple. |
| Variegatum | 18 | Do. |
| Bitter blue | 27 | Do. |

[1] Chromosome number determinations made on pollen mother cells.
[2] PI is the prefix letter designation assigned accessions that are collected by the Plant Introduction section of the United States Department of Agriculture.

Ea 6416 has a moderate olive green color [1] as mentioned above. The culms of Ea 6416 St. Augustine grass are compressed and branched. The flowering shoots are 5 to 15 centimeters tall. Blades are generally less than 5.8 centimeters long and over 8 millimeters wide.

Since environmental conditions such as climate and soil influence morphological characteristics to some degree, the morphological characteristics may vary slightly from locale to locale.

Morphological characteristics of Ea 6416 St. Augustine grass are compared to those of Floratine and Bitter Blue St. Augustine grasses in Table 2.

TABLE 2.—COMPARATIVE LEAF BLADE WIDTH AND LENGTH FOR Ea 6416 AND OTHER ST. AUGUSTINE GRASSES

| Selection/variety | Leaf blade width (mm)[1] | Leaf blade length (mm.) |
|---|---|---|
| Ea 6416 | [2] 8.23–8.63 | [2] 54.63–56.93 |
| Floratine | 7.28–7.72 | 60.99–64.61 |
| Bitter blue | 7.41–7.79 | 77.26–79.74 |

[1] Leaf blade width recorded one inch from leaf collar.
[2] Where Ea 6416 plants are maintained as a turf, the range of leaf blade length and width may not vary as much as indicated.

The horizontal growth rate of Ea 6416 St. Augustine grass, as reflected in rate of establishment, is significantly higher than those of Texas common, Floratine, and PI 243552 varieties of St. Augustine grass. This was found to be true for widely separated geographical areas where climatic and soil conditions differ. The horizontal growth rate of Ea 6416 is compared with the growth rates of Texas common, Floratine, and PI 243552 in Tables 3 and 4. All plots were identically planted. The observations in Table 3 were made approximately the middle of August from plots sprigged in the first week of May.

[1] The ISCC-NBS method of designating colors described in National Bureau of Standards Circular No. 553. The designated color is that of plants grown under field conditions. The Munsell color designation of Ea 6416 St. Augustine grass will range from 6.5 GY 4.0/3.8 to 6.5 GY 4.2/3.5 for a typical sample. These values are subject to some variation from sample to sample depending upon the specific conditions under which the sample is grown, etc.

TABLE 3.—RELATIVE COMPARISON OF PERCENT TURF COVER OF Ea 6416 ST. AUGUSTINE GRASS AND TEXAS COMMON ST. AUGUSTINE GRASS AT ROSENBURG, TEXAS

| Selection/variety | Percent area covered |
|---|---|
| Ea 6416 | 80 |
| Texas common | 67 |
| LSD 10% | 11 |

TABLE 4.—RELATIVE COMPARISON OF PERCENT TURF COVER OF Ea 6416 ST. AUGUSTINE GRASS, FLORATINE, AND PI 243552 ST. AUGUSTINE GRASSES PLANTED AT APOPKA, FLORIDA

| Selection/variety | Date | | | |
|---|---|---|---|---|
| | Mid-August [1] | | Mid-October [2] | |
| | Percent area covered | | | |
| | T | UT | T | UT |
| Ea 6416 | 77 | 57 | 93 | 78 |
| PI 243552 | 33 | 23 | 57 | 45 |
| Floratine | 40 | 23 | 57 | 47 |
| LSD 5% | 23 | NS | 20 | 16 |

[1] 246 days after planting.
[2] 308 days after planting.
T=plots treated with nematocide; UT=plots not treated with nematocide.

As shown above a new turf can be established twice as fast with Ea 6416 St. Augustine grass as with Floratine or PI 243552 varieties of St. Augustine grasses.

The data in Table 5 shows the low level of chinch bug infestation in plots of Ea 6416 St. Augustine grass as compared to the level in plots of Floratine St. Augustine grass in the same locale. Ratings on damage are also given in the table. Table 6 compares the chinch bug populations of and turf damage to Ea 6416 and other St. Augustine grasses in tests conducted during a different growing season. Again, all plots were in the same locale.

TABLE 5.—CHINCH BUG POPULATIONS AND TURF DAMAGE CAUSED BY CHINCH BUGS TO Ea 6416 ST. AUGUSTINE GRASS AND FLORATINE ST. AUGUSTINE GRASS AT APOPKA, FLORIDA

| Selection/variety | Chinch bug population [1] | Turf Damage [2] |
|---|---|---|
| EA 6416 | 11.3 | 1.7 |
| Floratine | 25.0 | 5.3 |
| LSD 5% | 11 | ---------- |

[1] Chinch bug counts per ⅔ square foot.
[2] Turf damage: 10-turf completely killed to 1-no visible injury to turf.

TABLE 6.—CHINCH BUG POPULATIONS AND TURF DAMAGE CAUSED BY CHINCH BUGS TO Ea 6416 ST. AUGUSTINE GRASS AND OTHER ST. AUGUSTINE GRASSES AT APOPKA, FLORIDA

| Selection/Variety | Chinch Bug Population [1] | Turf Damage [2] | Turf Quality |
|---|---|---|---|
| Ea 6416 | 2 | 1.5 | Good. |
| Floratine | 47 | 5.0 | Poor. |
| Variegatum | 89 | 8.0 | Very poor. |
| PI 243552 | 126 | 9.0 | Do. |

[1] Chinch bug counts per ⅔ square foot.
[2] Turf damage: 10-turf completely killed to 1-no visible turf injury.

The resistance of Ea 6416 St. Augustine grass to chinch bugs is significantly higher than that of Floratine, Variegatum and PI 243552 St. Augustine grasses irrespective of locale as shown in Tables 5 and 6 above. There was scarcely any injury from chinch bugs to Ea 6416 as compared to Floratine, Variegatum and PI 243552 which were all severely damaged by chinch bugs.

The degree of resistance of Ea 6416 to sting nematodes as reflected in the rate of establishment of plots not treated with nematocide as contrasted to plots treated with nematocide, is greater than that of Floratine and PI 243552 varieties of St. Augustine. The resistance of Ea 6416 to nematodes is compared with the resistance of Floratine and PI 243552 in Table 7. All plots were identically planted. Observations were made 246 days after sprigging. All plots were in the same locale.

TABLE 7.—RELATIVE COMPARISON OF PERCENT NEMATODE RESISTANCE OF Ea 6416 AND OTHER ST. AUGUSTINE GRASSES, APOPKA, FLA.

| Selection/variety: | Percent nematode resistance observed |
|---|---|
| Ea 6416 | 74 |
| Floratine | 58 |
| PI 243552 | 70 |

The resistance of Ea 6416 St. Augustine grass to nematodes is comparably greater than that of Floratine and PI 243552 St. Augustine grasses as shown in the above table.

Ea 6416 St. Augustine grass reproduces and propagates vegetatively by propagules. This results in the production of uniform plants retaining the parental characteristics.

What is claimed and desired to be secured by Letters Patent is:

1. A variety of St. Augustine grass plant, substantially as shown and described herein, characterized particularly by resistance to chinch bug and nematode damage, vigorous horizontal growth, stocky leaf blades, a moderate olive green color and ease of propagation.

No references cited.

ROBERT E. BAGWILL, *Primary Examiner.*